US010282875B2

(12) United States Patent
Chen et al.

(10) Patent No.: US 10,282,875 B2
(45) Date of Patent: May 7, 2019

(54) GRAPH-BASED ANALYSIS FOR BIO-SIGNAL EVENT SENSING

(71) Applicant: Internaitonal Brusiness Machines Corporation, Armonk, NY (US)

(72) Inventors: Chia-Yu Chen, White Plains, NY (US); Pei-Yun S. Hsueh, Hawthorne, NY (US); Jui-Hsin Lai, White Plains, NY (US); Yinglong Xia, Rye Brook, NY (US)

(73) Assignee: International Business Machines Corporation, Armonk, NY (US)

( * ) Notice: Subject to any disclaimer, the term of this patent is extended or adjusted under 35 U.S.C. 154(b) by 109 days.

(21) Appl. No.: 14/966,693

(22) Filed: Dec. 11, 2015

(65) Prior Publication Data

US 2017/0169591 A1 Jun. 15, 2017

(51) Int. Cl.
| | |
|---|---|
| *G06T 11/20* | (2006.01) |
| *A61B 5/00* | (2006.01) |
| *A61B 5/0205* | (2006.01) |
| *A61B 5/021* | (2006.01) |
| *A61B 5/024* | (2006.01) |

(Continued)

(52) U.S. Cl.
CPC .............. *G06T 11/206* (2013.01); *A61B 5/00* (2013.01); *A61B 5/02055* (2013.01); *A61B 5/7221* (2013.01); *A61B 5/7246* (2013.01); *A61B 5/746* (2013.01); *A61B 5/0022* (2013.01); *A61B 5/021* (2013.01); *A61B 5/024* (2013.01); *A61B 5/04012* (2013.01); *A61B 5/14542* (2013.01); *A61B 5/7264* (2013.01); *A61B 2503/12* (2013.01); *A61B 2505/07* (2013.01)

(58) Field of Classification Search
CPC ................... G06T 11/206; G06T 2207/20064
See application file for complete search history.

(56) References Cited

U.S. PATENT DOCUMENTS

| | | |
|---|---|---|
| 5,150,716 A | 9/1992 | Franssen et al. |
| 6,820,037 B2 | 11/2004 | Simon |

(Continued)

FOREIGN PATENT DOCUMENTS

| | | |
|---|---|---|
| EP | 2030565 B1 | 5/2013 |
| WO | 0140261 A1 | 6/2001 |

(Continued)

OTHER PUBLICATIONS

C.S. Yajnik et al., "Screening of Cardiovascular Autonomic Neuropathy in Patients with Diabetes Using Non-Invasive Quick and Simple Assessment of Sudomotor Function," Diabetes & Metabolism, Apr. 2013, pp. 126-131, vol. 39, No. 2.

(Continued)

*Primary Examiner* — Gregory J Tryder
*Assistant Examiner* — Michael Le
(74) *Attorney, Agent, or Firm* — Rahan Uddin; Ryan, Mason & Lewis, LLP

(57) ABSTRACT

One or more biological signals are obtained. The one or more biological signals are converted to one or more graph structures. Correlation between two or more of the biological signals are determined using the one or more graph structures. One or more changes in the one or more graph structures within a time window are recorded. A signal graph model is generated based on the recorded changes.

17 Claims, 8 Drawing Sheets

(51) Int. Cl.
*A61B 5/04* (2006.01)
*A61B 5/145* (2006.01)

(56) References Cited

U.S. PATENT DOCUMENTS

| | | |
|---|---|---|
| 7,087,015 B1 | 8/2006 | Comrie et al. |
| 7,344,853 B2 | 3/2008 | Giulian |
| 7,602,301 B1 | 10/2009 | Stirling et al. |
| 8,428,673 B2 | 4/2013 | Cho et al. |
| 8,512,240 B1* | 8/2013 | Zuckerman-Stark ........................ G16H 50/30 600/301 |
| 8,687,689 B2 | 4/2014 | Baraniuk et al. |
| 8,819,078 B2 | 8/2014 | Roy et al. |
| 2003/0105558 A1 | 6/2003 | Steele |
| 2004/0166536 A1 | 8/2004 | Kerkman et al. |
| 2005/0142524 A1 | 6/2005 | Simon et al. |
| 2005/0145187 A1 | 7/2005 | Gray |
| 2007/0078966 A1 | 4/2007 | Bromley |
| 2007/0197932 A1 | 8/2007 | Feke et al. |
| 2008/0214902 A1* | 9/2008 | Lee .......... A61B 5/16 600/301 |
| 2009/0149721 A1 | 6/2009 | Yang |
| 2009/0227881 A1* | 9/2009 | Reichman .......... A61B 5/0261 600/506 |
| 2011/0055924 A1* | 3/2011 | Stakhanova .......... G06F 21/55 726/23 |
| 2011/0066043 A1* | 3/2011 | Banet .......... A61B 5/022 600/485 |
| 2011/0221671 A1 | 9/2011 | King, III et al. |
| 2011/0222745 A1 | 9/2011 | Osterhout et al. |
| 2011/0257555 A1* | 10/2011 | Banet .......... A61B 5/0809 600/538 |
| 2012/0010522 A1 | 1/2012 | Knudsen et al. |
| 2012/0094395 A1 | 4/2012 | Sattler et al. |
| 2012/0165695 A1 | 6/2012 | Kidmose et al. |
| 2012/0172682 A1* | 7/2012 | Linderman .......... A61B 5/0476 600/301 |
| 2012/0238856 A1 | 9/2012 | Kidmose et al. |
| 2012/0252693 A1 | 10/2012 | Umansky et al. |
| 2013/0029998 A1 | 1/2013 | Mayanil et al. |
| 2014/0148657 A1* | 5/2014 | Hendler .......... A61B 5/0476 600/301 |
| 2014/0194761 A1 | 7/2014 | Lee et al. |
| 2014/0218226 A1 | 8/2014 | Raz et al. |
| 2016/0043819 A1* | 2/2016 | Eriksson .......... H04H 60/46 702/19 |
| 2017/0035351 A1* | 2/2017 | Prerau .......... G16H 50/30 |

FOREIGN PATENT DOCUMENTS

| | | |
|---|---|---|
| WO | 0211102 A1 | 2/2002 |
| WO | 03015059 A1 | 2/2003 |
| WO | 03073211 A2 | 9/2003 |
| WO | 2004043462 A1 | 5/2004 |
| WO | 2004073485 A2 | 9/2004 |
| WO | 2006020269 A3 | 2/2006 |
| WO | 2011011811 A1 | 2/2011 |
| WO | 2012097872 A1 | 7/2012 |
| WO | 2012175672 A2 | 12/2012 |
| WO | 2013026481 A1 | 2/2013 |
| WO | 2013064702 A2 | 5/2013 |
| WO | 2013116589 A1 | 8/2013 |

OTHER PUBLICATIONS

J.-C. Sagot et al., "Ergonomics in Product Design: Safety Factor," Safety Science, Mar. 2003, pp. 137-154, vol. 41, No. 2.

* cited by examiner

100

200

SIGNAL GRAPH AT t    SIGNAL GRAPH AT t+1    SIGNAL GRAPH AT t+2

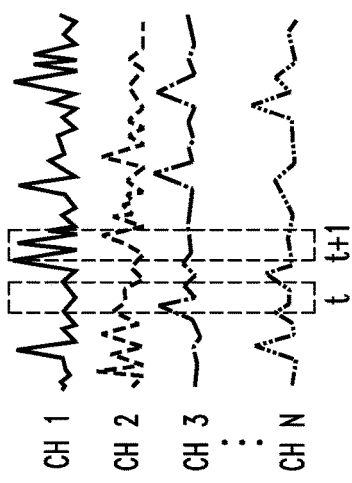
FIG. 5A
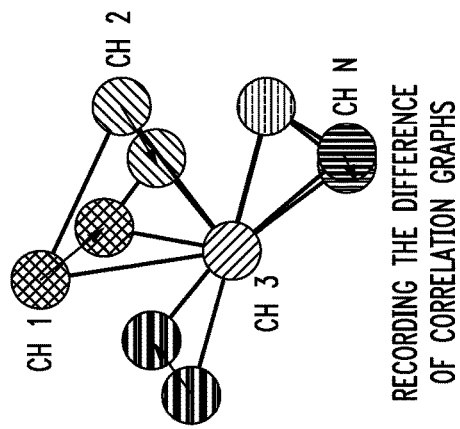
FIG. 5D RECORDING THE DIFFERENCE OF CORRELATION GRAPHS
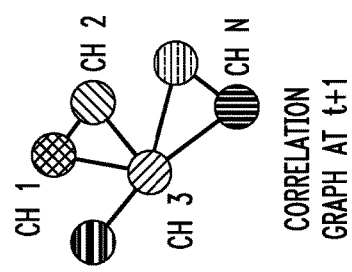
FIG. 5C CORRELATION GRAPH AT t+1
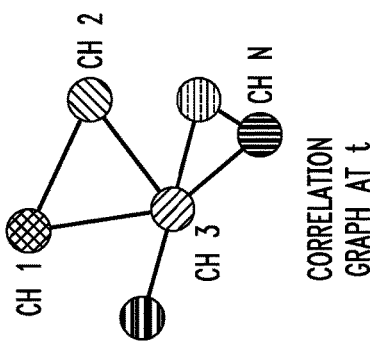
FIG. 5B CORRELATION GRAPH AT t

GRAPH-BASED ANALYSIS FOR BIO-SIGNAL EVENT SENSING

BACKGROUND

Monitoring of physiological parameters is an important aspect in evaluating and predicting the health status of individuals. Advances in the field of electronics over the past years have brought about significant changes in medical diagnostic and monitoring equipment, including arrangements for self-care monitoring of various health-related conditions (e.g., diabetes, arrhythmia, epilepsy). Individuals are now able to use wearable devices for monitoring various parameters, such as, temperature, respiration, blood pressure, blood glucose level, etc. These wearable devices provide for a new approach in continuous monitoring of patient health even when the patient is outside a medical facility. Additionally, the wearable devices also provide for health and wellness optimization in healthy people. These wearable sensors and devices used for remote health monitoring are becoming smaller and lighter for portability and convenience.

SUMMARY

Embodiments of the invention provide techniques for graph-based analysis of biological signals ("bio-signals").

For example, in one embodiment, a method comprises the following steps. One or more biological signals are obtained. The one or more biological signals are converted to one or more graph structures. Correlation between two or more of the biological signals are determined using the one or more graph structures. One or more changes in the one or more graph structures within a time window are recorded. A signal graph model is generated based on the recorded changes.

BRIEF DESCRIPTION OF THE DRAWINGS

FIGS. 5A-5D illustrate an exemplary signal correlation processing using one or more graph structures, according to an embodiment of the invention.

DETAILED DESCRIPTION

Figure 1:
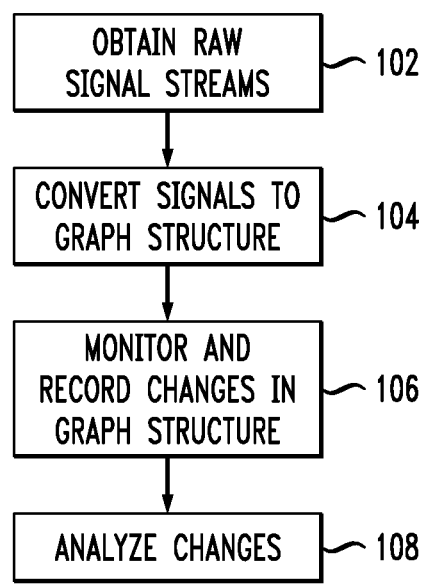
FIG. 1 illustrates an overview process of a methodology for obtaining and analyzing bio-signals using one or more graph structures, according to an embodiment of the invention.

Illustrative embodiments of the invention may be described herein in the context of illustrative methods, systems and devices for graph-based analysis of bio-signals. However, it is to be understood that embodiments of the invention are not limited to the illustrative methods, systems and devices but instead are more broadly applicable to other suitable methods, systems and devices. For Example, while embodiments described herein relate to bio-signals, other types of signals may also be processed using the systems and methods described herein.

At present, there is a growing trend towards self-monitoring at home on a daily basis to give medical providers visibility into patient status so that health status can be optimally maintained, exacerbations of chronic conditions can be ameliorated early, and episodic hospitalization can be avoided. Self-monitoring may be effective for lifestyle intervention and personalized intervention/adaptation. For example, continuous neural activity detection can augment existing applications with a finer-grained understanding of brain activity, such as, for detecting post-traumatic stress disorder and depression. As another example, self-monitoring may be useful for pain medication management, dosage assessment, and addiction alerting. Self-monitoring can also be useful in detecting and/or impeding migraines, cluster headaches, and facial pain attacks.

Wearable devices have grown in popularity as a means for providing suitable monitoring for this new approach to patient care, as well as health and wellness optimization in healthy people. As used herein, "wearable devices" may refer to devices which incorporate electronics, software, sensors and connectivity to enable the device to capture and exchange data with one or more other devices and/or databases. For example, a wearable device may be a smartwatch, a health monitor/sensor, smart contact lenses, etc. Wearable devices may be used to capture and record biological data (e.g., physiological data and/or pathological data) obtained from sensors attached to a person. The biological data may include bio-signals related to, for example, pulse, temperature, respiration, blood pressure, blood oxygen, electrocardiogram (EKG), etc. As used herein, bio-signals may refer to one or more signals generated from biological activities in the body (e.g., a human body) that may be measured and monitored. The wearable devices may also be configured to process the raw signals obtained from the sensors and transmit them to a remote location, such as a medical office or server.

However, as the size of the wearable devices tend to be small, the battery capacity of these wearable devices are also limited. Consequently, the length of time the device can be used continuously and the computational capacity of the devices may be limited. As such, continuous sensing may pose challenges to existing multi-modal analysis techniques using wearable devices. For example, detection of brain order-disorder transitions may use 20 dry electrodes embedded into a head cap, while all data uses an FCz reference and a 200 Hz sampling frequency. Analysis may include discovering temporal pattern of each channel from past sensor data, computing current temporal patterns of each channel from real-time sensor data, and capturing the differences by comparing the patterns across all channels. Furthermore, cross-validation may add additional computational burden. However, existing wearable devices are limited in their ability to handle computationally expensive and complex data analyses, such as detection of brain order-disorder transitions. As such, wearable devices can benefit from better compressive sensing capabilities that focus on capturing the structure of events.

Advantageously, embodiments herein provide methods and systems for graph-based computation for bio-signal event sensing by: (i) finding correlation of sensors and representing them as one or more dependency graphs to reduce computational and communication costs, wherein the correlation can include, but are not limited to, temporal concurrent correlation, temporal sequential correlation, and spatial correlation; (ii) exploring both appearance and temporal relations and mapping them into certain events with domain knowledge; (iii) model the event with one or more graph structures; and (iv) matching the graph structure of an incoming event to a graph structure database to identify a source of the bio-signal and/or potential medical conditions.

Referring to the figures, FIG. 1 depicts an overview of a methodology 100 for obtaining and converting bio-signals to one or more graph structures, according to an embodiment. At step 102, one or more raw signal streams (e.g., continuous streams of physiological signals) are obtained. The raw signals may include signals originating from the heart, the bowel, the pharynx, the trachea, one or more large airways, one or more small airways of a subject, etc. The one or more bio-signals may be captured using one or more sensors placed on and/or within a subject (e.g., a human subject or an animal subject). Then at step 104, the raw signals may be converted to one or more graph structures at a computing device, such as a wearable device or a remote computing system, suitable for performing the conversion according to embodiments herein. Then at step 106, changes in the graph structure are monitored and recorded. At step 108, the recorded changes may be analyzed manually by a user (e.g., a physician) or automatically by a computing device. The computing devices used herein may be, for example, but not limited to, a smart watch, a portable health monitoring device, a mobile phone, a tablet, a computer, etc.

Figure 2:
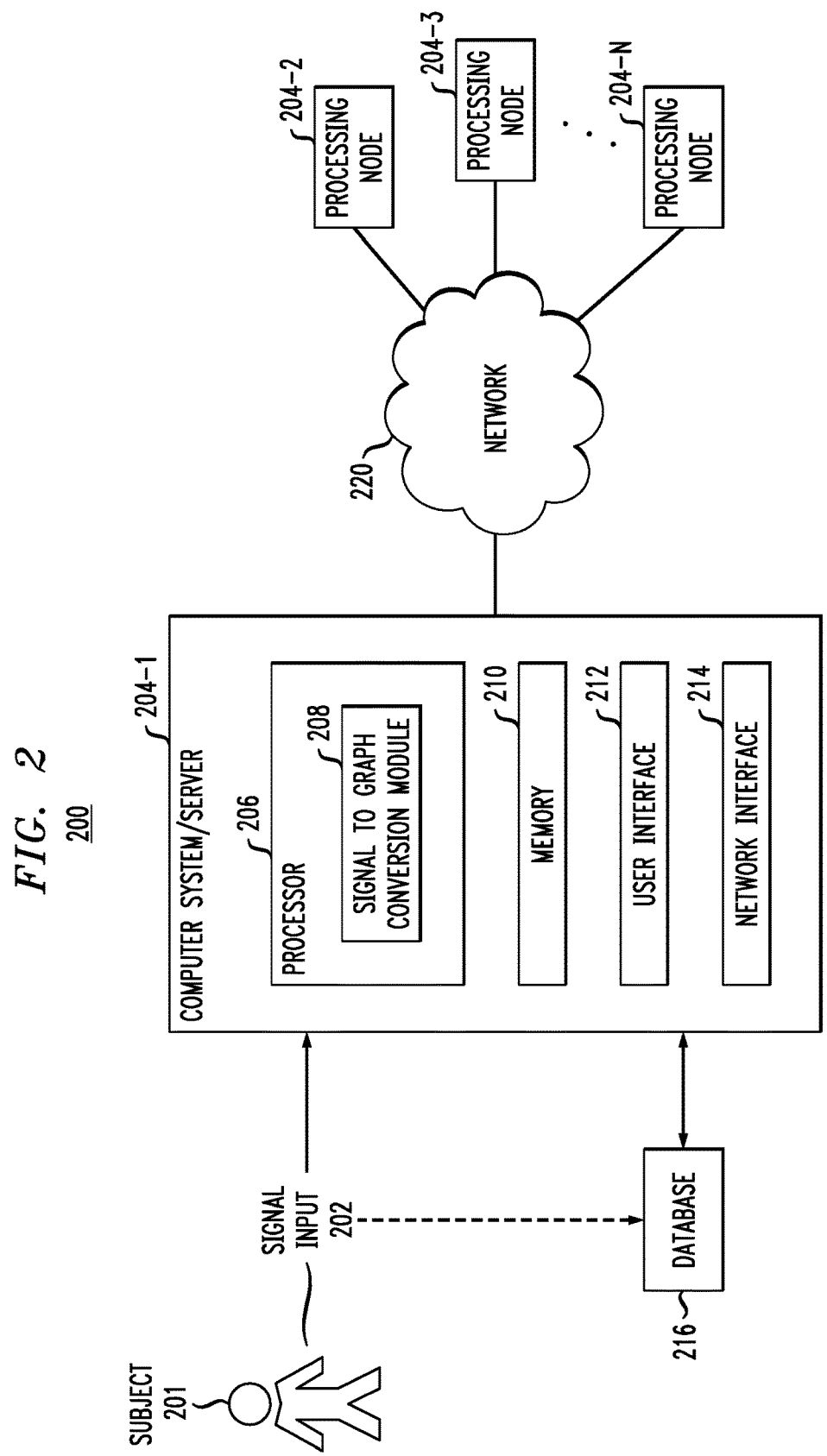
FIG. 2 illustrates an exemplary embodiment of a system for implementing the methodology of FIG. 1.

FIG. 2 depicts a system 200 for implementing methodology 100 of FIG. 1.

System 200 processing nodes 204-1 . . . 204-N, configured to communicate over a network 220. Each of processing nodes 204-1 . . . 204-N may be configured as shown in computer system/server 204-1, which may include, but is not limited to, wearable devices, personal computer systems, server computer systems, thin clients, thick clients, handheld or laptop devices, multiprocessor systems, microprocessor-based systems, programmable consumer electronics, network PCs, minicomputer systems, mainframe computer systems, and distributed cloud computing environments that include any of the above systems or devices, and the like. Computer system/server 204-1 may include one or more processors 206 coupled to a memory 210, a user interface 212 and a network interface 214. Processor 206 may comprise a signal to graph conversion module 208 for implementing one or more steps of methodology 100 of FIG. 1. User interface 212 may be configured to enable user input into the computer system/server 204-1. Network interface 214 may be configured to enable the computer system/server 204-1 to interface with a network and other system components.

The computer system/server 204-1 may be configured to obtain and/or receive signal input 202 from one or more sensors attached to subject 201 and/or from a database 216. Database 216 may store one or more raw data signals, and/or store results from the analyses performed by signal to graph conversion module 208. Data may periodically be transmitted between subject 201, database 216 and the one or more processing nodes 204-1 . . . 204-N via network 220. Network 220 may be a communication link comprising an internet connection, Ethernet link, local area link, cellular link, satellite link, global system for mobile communication (GSM), etc. It is to be appreciated that system 200 may include more or less components than shown in FIG. 2. For example, system 200 may include multiple ones of database 216, signal input 202 and may also include additional components suitable for implementing methodology 100 of FIG. 1.

Figure 3A:
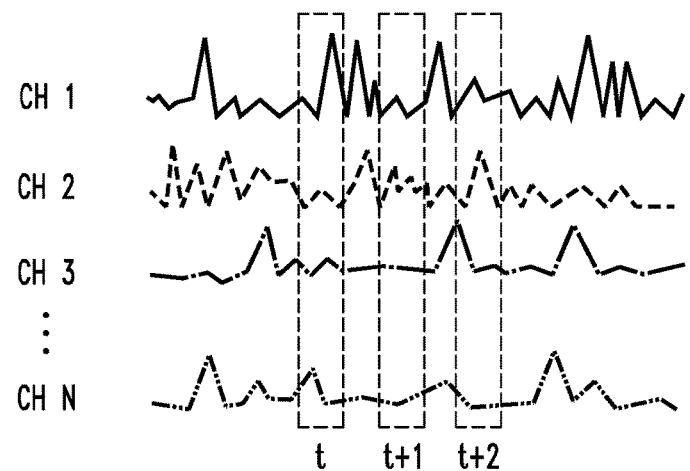
FIG. 3A illustrates an exemplary set of bio-signals for use in the methodology of FIG. 1.

FIG. 3A depicts an illustrative set of bio-signals from one or more sensors, represented as channels 1 . . . N. The bio-signals of channels 1 . . . N may be collected as raw data in real-time. For example, the bio-signals may correspond to heart rate and respiration rate extracted from a raw EKG signal, and core body temperature extracted from skin temperature. The bio-signals may be monitored for changes according to pre-determined time windows defined between time indices, such as time indices t, t+1 and t+2, etc. The duration of the time windows may be specified by a medical provider, a user of a wearable device, or automatically by a module implemented within the device capturing the bio-signals.

Figure 3B:
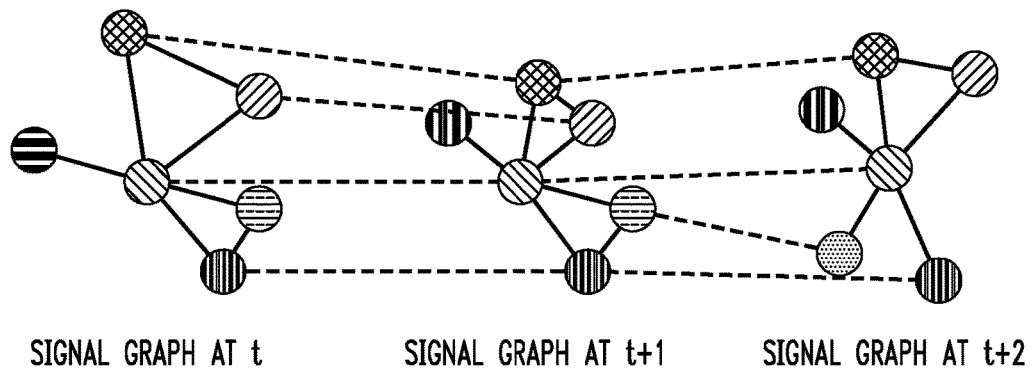
FIG. 3B illustrates an exemplary graph structure representation of the bio-signals of FIG. 3A.

FIG. 3B shows an illustrative graph structure representation of the bio-signals of channels 1 . . . N of FIG. 3A at time indices t, t+1 and t+2, respectively. Notably, embodiments herein represent bio-signals (e.g., physiological signals) with one or more signal-graphs with high-dimension (HD) structure. Each graph node, symbolized by a circle, within a signal-graph structure represents one bio-signal or channel; each solid link represents appearance correlation (e.g., correlation of waveforms) between two nodes; each dashed link represents temporal correlation for one node over time, or in the case when a new node is appearing, the new node's correlation with one or more old nodes may also be detected; and the pair-wise correlation is represented by the length of a link between two nodes at each time stamp. The graph structures model signal distribution on spatial and temporal domain, thereby reducing computational complexity via graph processing. The one or more bio-signals can be converted to graph structure in real-time, or captured and stored for online computation at a server using the methodology described herein (e.g., capture more signals for conversion to graph structures and subsequent analysis as online server may have more processing power for comparisons)

While the signals depicted in FIGS. 3A and 3B are associated with one subject, alternative embodiments may obtain one or more signals from multiple subjects. Certain embodiments herein may be useful in analyzing community health using signals obtained from multiple subjects. Furthermore, conversion of the signals to graph structure and further analysis may be performed at a backend server in certain instances involving large numbers of signals.

Advantageously, various embodiments of the invention provide for comparison of the data by comparing changes in the graph structures within specified time windows, instead of checking the channels pair-by-pair. As such, the data (e.g., the graph structures) may be more compressed than the raw signals, thereby increasing computational efficiency and reducing power consumption at the processing device (e.g., the wearable device).

Figure 4A:
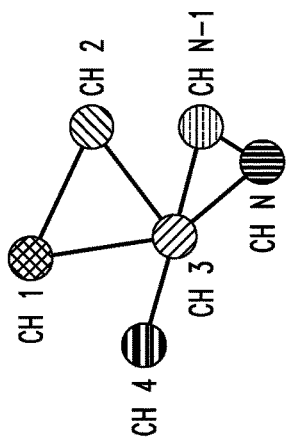
FIGS. 4A-4C illustrate exemplary steps in modeling the bio-signals of FIG. 3A as one or more signal graphs, according to an embodiment of the invention.
Figure 4B:
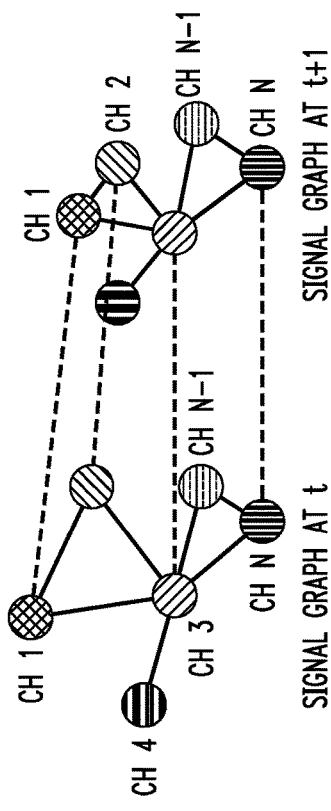
Figure 4C:
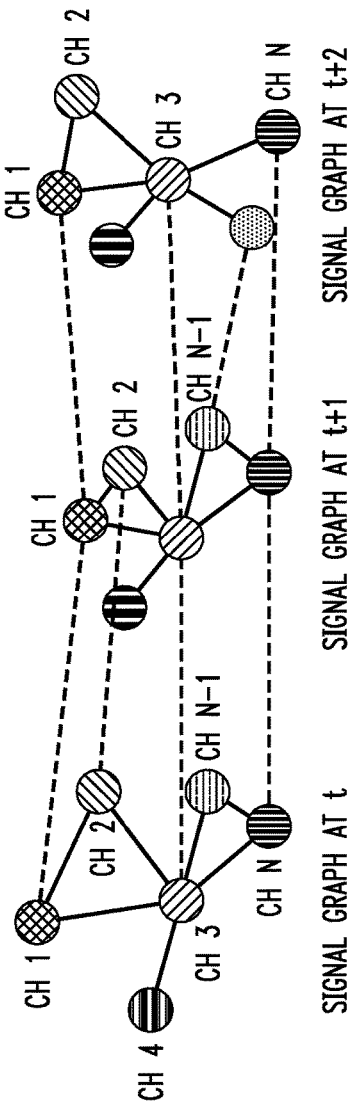

FIGS. 4A, 4B and 4C illustrate steps in modeling bio-signals as signal-graphs, according to an embodiment of the invention. As noted earlier, each solid link represents the appearance correlation (e.g., correlation of waveforms) between two nodes, and each dashed link represents the temporal correlation between two nodes.

As shown in FIG. 4A, obtained bio-signals, such as those shown in FIG. 3A, are processed to calculate appearance correlations of each time index t (e.g., at time t, t+1, t+2, etc). In this step, one or more possible correlations (i.e., some or all possible correlations) are calculated for a window of time. For example, given two channels such as channel 1 and channel 2, the signal variation can be analyzed and their correlation can be calculated using an appropriate equation, for example, the Pearson product-moment correlation coefficient. For each time window, all signals can be analyzed to find some or all possible correlations between the signals. Signals with correlation exceeding a specific confidence threshold (e.g., greater than 90%) may be stored in a remote database and/or a wearable device, while uncorrelative signals having correlation below the specific confidence threshold are discarded. Notably, the length of the links is inversely proportional to correlation, such that the shorter the length of the link between two nodes, the stronger the correlation is between the two notes. Illustratively, the link length between channel N−1 and channel N is shorter than that between channel 1 and channel 2, which may indicate that the appearance correlation between channel N−1 and channel N is stronger than that between channel 1 and channel 2.

As shown in FIG. 4B, at the next step, the temporal correlation of the signals between a first time index and a second time index is calculated, e.g., a temporal correlation between time t and t+1, between t+1 and t+2, between t and t+2, etc. In this step, one or more signal correlations are calculate for some or all the nodes during each time span using, for example, an appropriate equation. Again, the link length is inversely proportional to the correlation between two nodes. Illustratively, the link length between channel 1 at time indices t and t+1 is longer than that between channel 3 during the same time window of time indices t and t+1, which may indicate that the temporal correlation of channel 1 for the time window defined by time indices t and t+1 is weaker than the temporal correlation of channel 3 for the same time window.

Then at the next step, as shown in FIG. 4C, a model can be generated from the one or more graph structures. Advantageously, the model can be extend to a high-dimension structure for modeling the signals in spatial and temporal distribution. As shown in FIG. 4C, a model may comprise a series of graph structures showing the appearance correlation and temporal correlation of the one or more signals at each time window. For example, from time t to t+1 and from t+1 to t+2, the change in distance between the nodes can be observed. This change in length of the links may be an indication of correlations between the channels becoming stronger/weaker. Furthermore, an event may be modeled using a series of signal graphs such that changes in correlation between the nodes can be observed. When the graph changes, the underlying signal corresponding to the node may be extracted. The extracted signal may be compared to one or more patterns stored at a library/database. If the change matches certain patterns stored in the library, such as database 216, the signal can be recognized as being associated with a specific source (e.g., a signal from the heart) and/or condition (e.g., arrhythmia). In various embodiments, a library of specific patterns can be created, such that if the change in the graph structure matches the pattern(s) in the library, a message and/or an alert can be triggered automatically and transmitted to a device of a healthcare provider and/or a caregiver.

For example, a subject may be monitored for an event as prescribed by a physician, such as epilepsy, for which abnormal signals correlating to abnormal neural activities may be observed at least five minutes before the onset of epilepsy. A device configured to implement an embodiment of the invention may receive one or more bio-signals, including neural signals, from one or more sensors attached to the subject and convert the signals into one or more graph structures. The graph structures are then monitored for changes as described above. The changes in the signals, as recorded in the changes in the graph structures, may be matched against the patterns stored in a library (e.g., database 216) and the device may efficiently determine the potential onset of epilepsy so as to send out an alert to a provider or care giver to take precautions in a timely manner.

FIGS. 5A, 5B, 5C and 5D depict an exemplary signal correlation using graph structures, according to an embodiment of the invention. As shown in FIG. 5A, a plurality of bio-signals are obtained in real-time, e.g., from a wearable device attached to a user or from a database. From the raw signals, a system implementing the methods described herein can convert and/or translate the raw signals to one or more graph structures. As the signals are collected continuously, the raw signals are also converted continuously in real time as they are received/collected. The raw signals may then be discarded after they are converted to one or more graph structures. This conversion to graph structure compresses the data significantly. Subsequently, by monitoring these graph structures for changes in space and time domains, the signals can be analyzed accordingly. Analysis of the changes is computationally less expensive than conventional methods of comparing the raw data channel to channel. As such, various embodiments herein may provide advantages over conventional methods as most wearable devices tend to be small and may have low computational power/capacity.

FIG. 5B and 5C illustrate exemplary graph structures of the raw signals of FIG. 5A at time index t and time index t+1. As shown, the graph structures of FIGS. 5B and 5C also include one or more appearance correlations between the nodes, represented by the solid links between the nodes. The appearance correlation may be determined in a manner similar to that described above in the context of FIG. 4A. Conventionally, for each of the channels, the waveform and the recorded length in windows have to be monitored and compared. However, in various embodiments of the invention using graph structure representations, only the change (s) in the graph structures need to be monitored and recorded (e.g., change in distance or length of links between the nodes).

FIG. 5D illustrates an exemplary graph structure recording the difference in correlation of the graphs shown in FIGS. 5B and 5C. The changes in the nodes between time t and t+1 are represented as arrows in the graph structure of FIG. 5D. In each time span (e.g., sampling window), the signals may change and the corresponding graph structure would also change (e.g., connections in the graph structure may change). As shown in FIG. 5D, various embodiments herein provide a way to compare the node distance changes in time domain and represent the changes in correlation between channels. The change in correlation may be recorded from time to time, the frequency of recording the changes may vary based on application or preference.

Figure 6C:
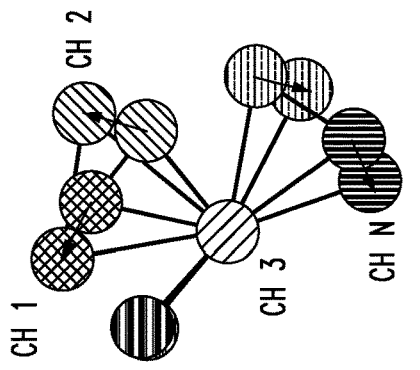
FIGS. 6A-6C illustrate exemplary steps in correlating bio-signals and recording changes in the bio-signals using one or more graph structures, according to an embodiment of the invention.
Figure 6B:
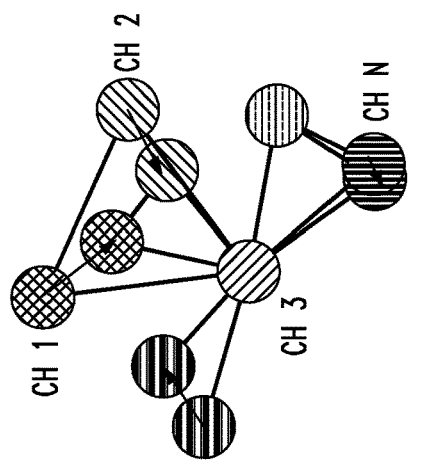
Figure 6A:
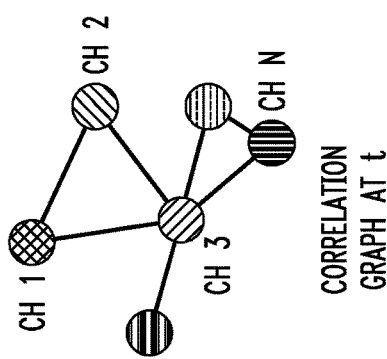

FIGS. 6A, 6B and 6C further delineate steps in correlating bio-signals using one or more graph structures, according to an embodiment of the invention. As shown in FIG. 6A, bio-signals that have been converted to a graph structure are processed to calculate signal correlations at each time index, wherein the link length is in inverse proportion to the correlation between the nodes. Conversion from bio-signals to graph structures and the subsequent calculation of correlations are described above in the context of FIGS. 4A-4C above.

Then, as shown in FIGS. 6B and 6C, the temporal correlation changes of the graph structures from one time index to the next time index (e.g., from t to t+1, t+1 to t+2) are recorded. The changes in the nodes are represented by arrows on each graph structure for each time span. Given an input of a plurality of signals, the output of systems implementing methodology 100 would be a series of dependency graphs, such as those shown in FIGS. 6B and 6C. Each dependency graph recording the change between time windows. Accordingly, depending on the granularity of the time windows, the number of dependency graphs reported would vary (e.g., shorter time windows, more graphs generated as output). The dependency graphs(s) may be sent to one or more devices for display and/or analysis by one or more users.

Various embodiments of the invention provide benefits in reduced computation, including: (1) reduced signal channels, where only the correlative/significant signals (e.g., signals with correlation exceeding a confidence threshold) are stored, and un-correlative signals ignored (e.g., discarding un-correlated information); (2) simplified signal complexity using graph structure, such that event detection can be performed by matching the signal distribution to signal-graph and using a look-up-table of patterns in a database; and (3) cross-validation made easy via fast discovery of cross-channel events and curation of events across users as event repositories for evidence and pattern generation. Furthermore, various embodiments herein also provide methods and systems to lower data size of transmissions by only transmitting graph changes (i.e., as only the graph changes are transmit instead of entire graphs) and preserving the significant information.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention. For example, computer system/server 204-1 may comprise a computer program product for implementing embodiments of the invention disclosed herein.

The computer readable storage medium (e.g., memory 210) can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network (e.g., network 220), including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is understood in advance that although this disclosure includes a detailed description on cloud computing below, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises. Public cloud: the cloud infrastructure is made available to the general public or a large industry group and is owned by an organization selling cloud services. Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Figure 7:
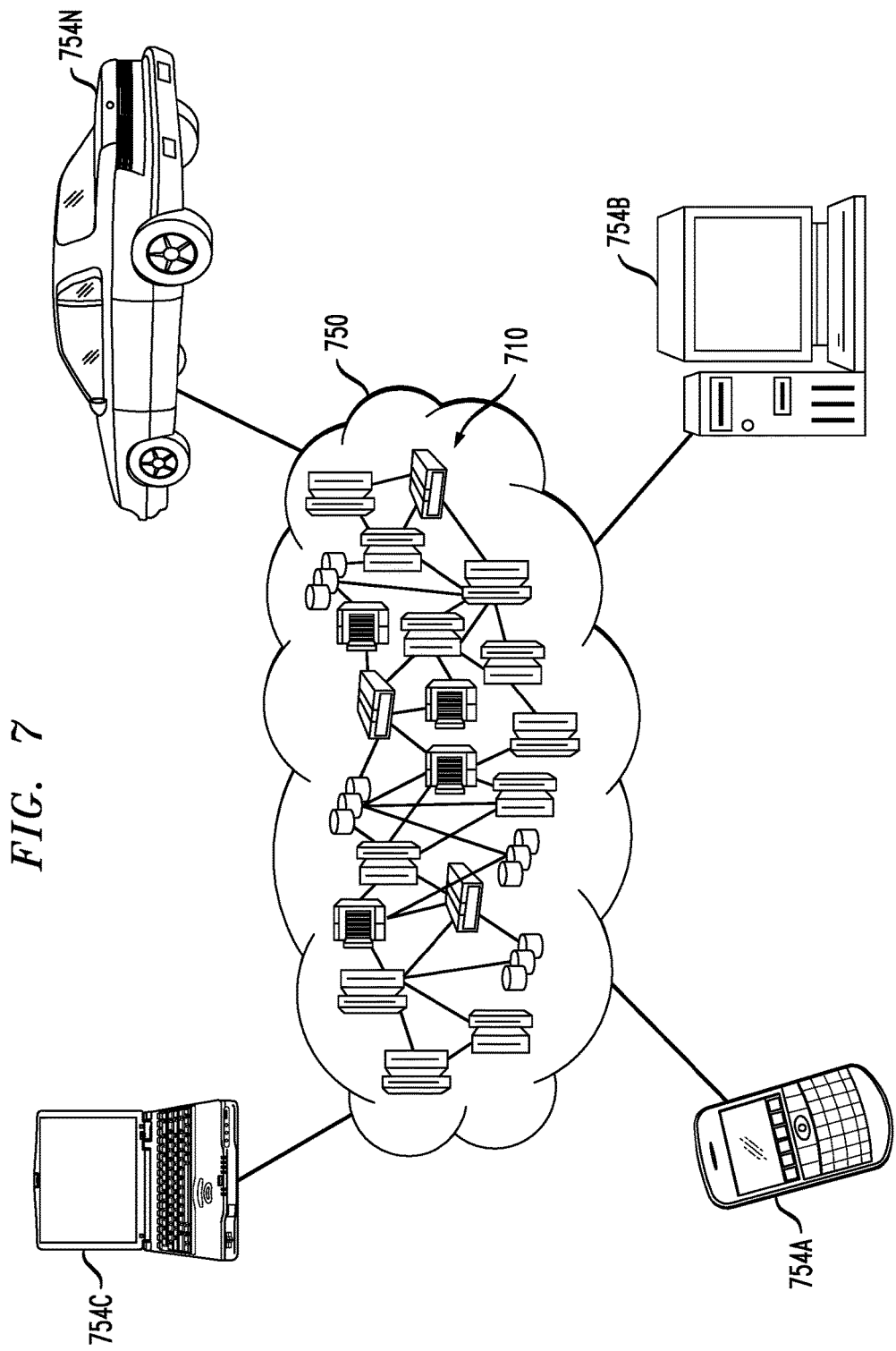
FIG. 7 illustrates a cloud computing environment, according to an embodiment of the invention.

Referring now to FIG. 7, illustrative cloud computing environment 750 is depicted. As shown, cloud computing environment 750 comprises one or more cloud computing nodes 710 with which local computing devices used by cloud consumers, such as, for example, a wearable device (not explicitly shown), a personal digital assistant (PDA) or cellular telephone 754A, desktop computer 754B, laptop computer 754C, and/or automobile computer system 754N may communicate. Nodes 710 may communicate with one another. They may be grouped (not shown) physically or virtually, in one or more networks, such as Private, Community, Public, or Hybrid clouds as described hereinabove, or a combination thereof. This allows cloud computing environment 750 to offer infrastructure, platforms and/or software as services for which a cloud consumer does not need to maintain resources on a local computing device. It is understood that the types of computing devices 754A-N shown in FIG. 7 are intended to be illustrative only and that computing nodes 710 and cloud computing environment 750 can communicate with any type of computerized device over any type of network and/or network addressable connection (e.g., using a web browser).

Figure 8:
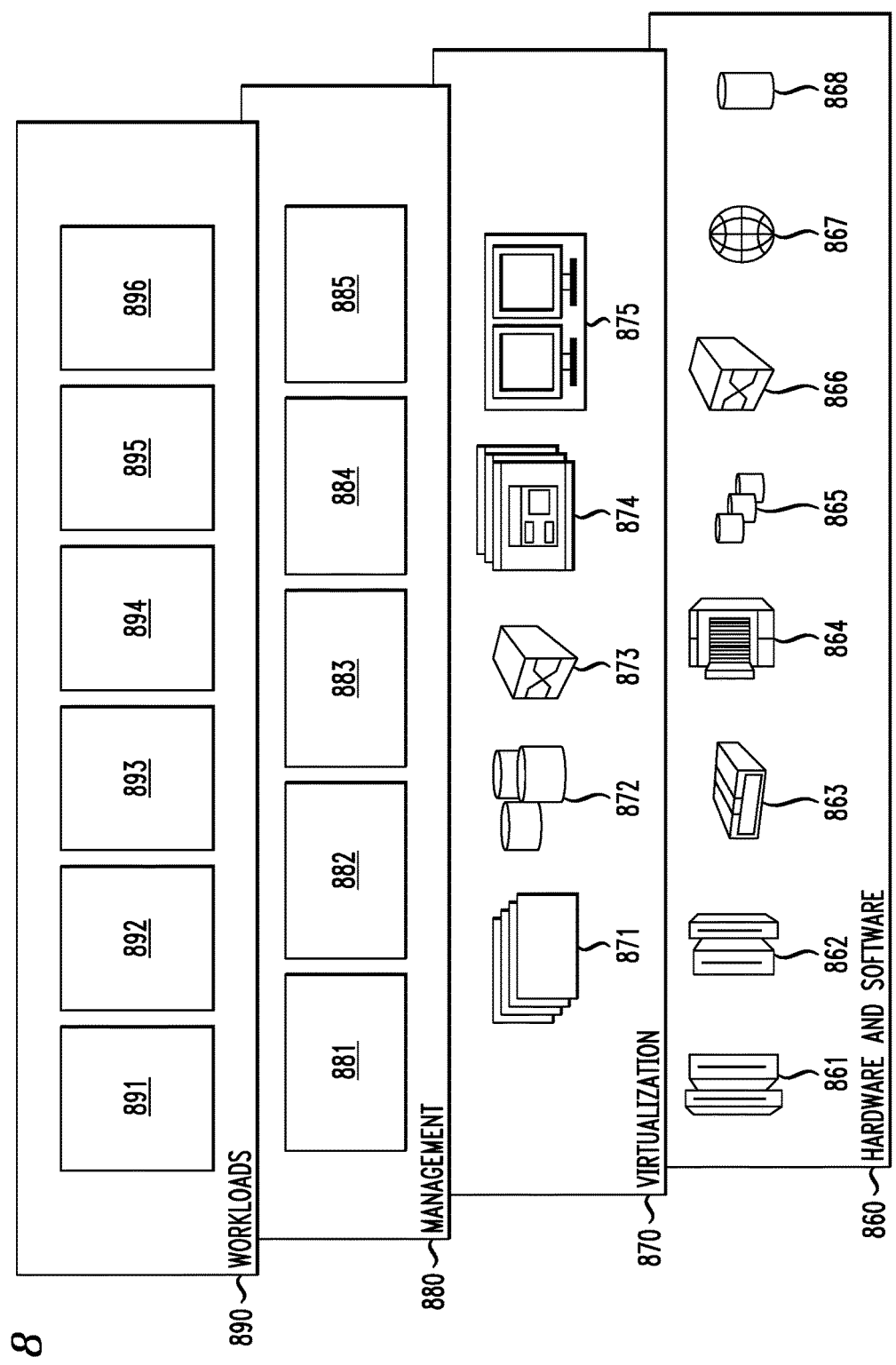
FIG. 8 depicts abstraction model layers according to an embodiment of the invention.

Referring now to FIG. 8, a set of functional abstraction layers provided by cloud computing environment 750 (FIG. 7) is shown. It should be understood in advance that the components, layers, and functions shown in FIG. 8 are intended to be illustrative only and embodiments of the invention are not limited thereto. As depicted, the following layers and corresponding functions are provided:

Hardware and software layer 860 includes hardware and software components. Examples of hardware components include: mainframes 861; RISC (Reduced Instruction Set Computer) architecture based servers 862; servers 863; blade servers 864; storage devices 865; and networks and networking components 866. In some embodiments, software components include network application server software 867 and database software 868.

Virtualization layer 870 provides an abstraction layer from which the following examples of virtual entities may be provided: virtual servers 871; virtual storage 872; virtual networks 873, including virtual private networks; virtual applications and operating systems 874; and virtual clients 875.

In one example, management layer 880 may provide the functions described below. Resource provisioning 881 provides dynamic procurement of computing resources and other resources that are utilized to perform tasks within the cloud computing environment. Metering and Pricing 882 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 883 provides access to the cloud computing environment for consumers and system administrators. Service level management 884 provides cloud computing resource allocation and management such that required service levels are met. Service Level Agreement (SLA) planning and fulfillment 885 provide pre-arrangement for, and procurement of, cloud computing resources for which a future requirement is anticipated in accordance with an SLA.

Workloads layer 890 provides examples of functionality for which the cloud computing environment may be utilized. Examples of workloads and functions which may be provided from this layer include: mapping and navigation 891; software development and lifecycle management 892; virtual classroom education delivery 893; data analytics processing 894; transaction processing 895; and graph-based analysis of biological signals 896, which may implement one or more of the functions described above.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, comprising the steps of:
obtaining one or more biological signals from one or more sensors attached to one or more subjects, wherein the one or more biological signals are associated with one or more signal channels;
converting the one or more biological signals into one or more graph structures, wherein each graph structure comprises one or more nodes representing respective ones of the one or more signal channels at a time index;
determining one or more correlations associated with the one or more signal channels using at least one of the one or more graph structures, wherein the one or more correlations comprise a correlation type selected from the group consisting of a temporal concurrent correlation, a temporal sequential correlation, and a spatial correlation;
recording one or more changes in the one or more correlations within at least one time window, wherein the at least one time window is defined based on at least one of the one or more time indices;
generating a signal graph model based on the one or more recorded changes;
determining one or more correlation confidence levels for the one or more correlations; and one of:
storing one or more of the one or more biological signals associated with a correlation confidence level exceeding a specified correlation confidence threshold; and
discarding one or more of the one or more biological signals associated with a correlation confidence level below a specified correlation confidence threshold; and
wherein the steps are performed by at least one processor device coupled to a memory.

2. The method of claim 1, further comprising comparing the one or more recorded changes to one or more patterns stored in a database.

3. The method of claim 2, further comprising generating at least one of a message and an alert in response to a match between the one or more recorded changes and a pattern for a medical condition stored in the database.

4. The method of claim 3, further comprising transmitting the at least one of the message and the alert to one or more devices.

5. The method of claim 1, wherein the one or more biological signals are obtained in real-time or near real-time from the one or more sensors.

6. The method of claim 5, wherein the one or more sensors are comprised within one or more wearable devices.

7. The method of claim 5, wherein the one or more biological signals are converted into the one or more graph structures in real-time or near real-time.

8. The method of claim 1, wherein determining the one or more correlations comprises determining one or more appearance correlations between two or more signal channels at a given time index.

9. The method of claim 1, wherein determining the one or more correlations comprises determining one or more temporal correlations, and wherein determining the one or more temporal correlations comprises determining a temporal correlation between a given signal channel at a first time index and the given signal channel at a second time index.

10. The method of claim 1, wherein the signal graph model comprises one or more dependency graphs.

11. The method of claim 1 further comprising displaying the signal graph model on one or more devices.

12. The method of claim 1, wherein the one or more graph structures are more compressed than the one or more biological signals.

13. An apparatus comprising:
a memory and a processor operatively coupled to the memory and configured to implement the steps of:
obtaining one or more biological signals from one or more sensors attached to one or more subjects, wherein the one or more biological signals are associated with one or more signal channels;
converting the one or more biological signals into one or more graph structures, wherein each graph structure comprises one or more nodes representing respective ones of the one or more signal channels at a time index;
determining one or more correlations associated with the one or more signal channels using at least one of the one or more graph structures, wherein the one or more correlations comprise a correlation type selected from the group consisting of a temporal concurrent correlation, a temporal sequential correlation, and a spatial correlation;
recording one or more changes in the one or more correlations within at least one time window, wherein the at least one time window is defined based on at least one of the one or more time indices;
generating a signal graph model based on the one or more recorded changes;
determining one or more correlation confidence levels for the one or more correlations; and one of:
storing one or more of the one or more biological signals associated with a correlation confidence level exceeding a specified correlation confidence threshold; and
discarding one or more of the one or more biological signals associated with a correlation confidence level below a specified correlation confidence threshold.

14. The apparatus of claim 13, wherein the processor is further configured to implement the steps of:
comparing the one or more recorded changes to one or more patterns stored in a database;
generating at least one of a message and an alert in response to match between the one or more recorded changes and a pattern for a medical condition stored in the database; and
transmitting the at least one of the message and the alert to one or more devices.

15. The apparatus of claim 13, wherein the one or more biological signals are obtained in real-time or near real-time from the one or more sensors.

16. The apparatus of claim 15, wherein the one or more sensors are comprised within one or more wearable devices.

17. A computer program product comprising a non-transitory computer readable storage medium for storing computer readable program code which, when executed, causes a computer to:
obtain one or more biological signals from one or more sensors attached to one or more subjects, wherein the one or more biological signals are associated with one or more signal channels;
convert the one or more biological signals to one or more graph structures, wherein each graph structure comprises one or more nodes representing respective ones of the one or more signal channels at a time index;
determine one or more correlations associated with the one or more signal channels using at least one of the one or more graph structures, wherein the one or more correlations comprise a correlation type selected from the group consisting of a temporal concurrent correlation, a temporal sequential correlation, and a spatial correlation;
record one or more changes in the one or more correlations within at least one time window, wherein the at least one time window is defined based on at least one of the one or more time indices;
generate a signal graph model based on the one or more recorded changes;
determine one or more correlation confidence levels for the one or more correlations: and one of:
storing one or more of the one or more biological signals associated with a correlation confidence level exceeding a specified correlation confidence threshold; and
discarding one or more of the one or more biological signals associated with a correlation confidence level below a specified correlation confidence threshold.

* * * * *